United States Patent [19]

Stewart

[11] Patent Number: 5,163,909
[45] Date of Patent: Nov. 17, 1992

[54] MEDICAL FLUID DELIVERY SYSTEM
[75] Inventor: Gene L. Stewart, San Diego, Calif.
[73] Assignee: Alan E. Jordan, Poway, Calif.
[21] Appl. No.: 646,804
[22] Filed: Jan. 28, 1991
[51] Int. Cl.$^5$ ............................................. A61M 37/00
[52] U.S. Cl. ..................................... 604/140; 604/131; 128/DIG. 12
[58] Field of Search ............... 604/140, 131, 141, 143, 604/146, 147, 148, 132; 128/DIG. 12

[56] References Cited

U.S. PATENT DOCUMENTS

| | | | |
|---|---|---|---|
| 4,684,367 | 8/1987 | Schaffer et al. | 604/140 |
| 4,784,652 | 11/1988 | Wikstrom | 604/141 |
| 4,857,055 | 8/1989 | Wang | 604/141 |
| 4,969,874 | 11/1990 | Michel et al. | 604/140 |
| 5,013,303 | 5/1991 | Tamari et al. | 604/140 |

FOREIGN PATENT DOCUMENTS 9004987  5/1990  World Int. Prop. O. ........ 604/143

Primary Examiner—Gene Mancene
Assistant Examiner—Michael Lynch
Attorney, Agent, or Firm—Frank D. Gilliam

[57] ABSTRACT

A compressed gas actuated, portable fluid delivery system including separate disposable components which provides multiple, precisely rate controlled administration of medical fluids to patients. A pressurization housing includes a holder for a liquid gas cylinder, a mechanism for piercing the cylinder and connecting the cylinder output in a sealed relationship to an output tube through pressure regulators and a pressure gauge. The pressurization housing includes a safety latch interconnected to a pressure on-off valve for preventing opening the housing while pressurized. The output tube leads to a pressure chamber in which a flexible bag containing a fluid to be delivered may be placed. Pressure within the chamber squeezes the bag, forcing fluid through a fluid output tube to, in seriatim, a particulate filter, a binary flow control valve assembly, an air eliminating filter and finally to a fitting adapted to connect to an administration device such as a hypodermic needle, nasal tube or the like. These various components may be included serially in several containers for ease of replacement or in a single unit, as desired.

12 Claims, 2 Drawing Sheets

MEDICAL FLUID DELIVERY SYSTEM

BACKGROUND OF THE INVENTION

This invention relates in general to devices for delivering fluids at precise selected flow rates and, more particularly, to systems for providing multiple, precisely rate-controlled administrations of medical fluids to patients.

Medical fluids have long been administered in the treatment of both human and animal patients. Typically, medical liquids have been introduced intravenously through tubes connecting a supply container to a hypodermic needle. These liquids include, for example, blood, saline solutions, glucose solutions and solutions containing various pharmaceuticals. Similarly, tubes running from supply containers may be introduced into the stomach, generally through the nose and gullet to supply nutrients, pharmaceuticals and the like. In some cases, tubes may be threaded into the lung for the administration of gases, mists, etc. in the treatment of some conditions.

In the past, these fluids were generally contained in a bottle or limp plastic bag hung from a support above the patient, with the force of gravity causing the fluid to move through a tube to the patient. Generally, the rate of flow was controlled by a valve device variably pinching the tube. Flow rate control with this arrangement was rather crude due to variations in flow control setting, changes in container elevation, changes in fluid head level as the fluid is used, etc. These systems were not vary portable, generally requiring a wheeled stand for the container to maintain the container height during patient movement. The height of the container above the administration site would undesireably change as a patient moved from a bed to a wheelchair or to walking.

While these systems are still widely used, attempts have been made to overcome the limitations and problems with them. Attempts have been made to pressurize the supply container with an internal or external gas-filled bladder to transmit pressure to the fluid in the container. Pressure would tend to decrease, however, during use since as the bladder expanded, the internal pressure decreased proportionately. Also, changes in ambient temperature would change bladder pressure.

More recently, a number of complex systems for maintaining flow rate in the delivery of medical fluids have been proposed. For example, Metcalf in U.S. Pat. No. 4,043,332 proposes to pressurize a supply container to a higher than delivery pressure, then use a flow regulator to reduce pressure and provide the desired flow rate. However, this system is capable of only limited flow rate adjustment, flow rate must be manually gradually adjusted, and flow rate cannot be quickly and accurately changed among several pre-selected rates, leading to possible errors in flow rate. Also, this device must still be hung from a support near the patient.

Other complex systems for administering medical fluids are described by Krakauer et al in U.S. Pat. No. 3,375,824, Dancy in U.S. Pat. No. 3,640,276 and Adelberg in U.S. Pat. No. 3,640,277. While each has unique features, none disclose a system having the desirable ability to quickly and precisely change flow rates among several different rates and all are large and cumbersome. Serious safety problems may be encountered if these devices are inadvertently opened during operation.

Thus, there is a continuing need for an improved medical fluid delivery system capable of providing a number of precisely selected flow rates in a compact easily portable system, with improved safety in the event of errors in the use of the system.

SUMMARY OF THE INVENTION

An object of this invention is, therefore, to provide a medical fluid delivery system overcoming the above-noted problems.

Another object is to provide a delivery system capable of providing any of a number of pre-selected precise flow rates. A further object is to provide a quick, convenient, safe and reliable mechanism for connecting pressurization means to the delivery system.

Yet another object is to provide a safety interlock to prevent the opening of the unit while in use.

Still a further object is to provide a delivery system made up of discrete disposable components for ease of use and replacement.

Still a further object of the invention is its simplicity of operation.

The above-noted objects, and others, are accomplished in accordance with this invention by a system which basically includes a first container housing the high pressure source, a pressure on-off valve and pressure regulators to reduce pressure to the desired level, a pressure chamber for holding at least one flexible medical fluid bag and pressurized by a tube from the first container, and a binary flow control device for selecting one of a number of preselected flow rates. The output from the flow control device is connected to conventional tubes, hypodermic needles or the like for administration of the medical fluid to the patient.

For optimum system performance and safety, a particulate filter is included in the medical fluid tube between the pressure chamber and the flow control device and an air eliminating filter is included in the outlet of the flow control device.

The first or pressure production container basically includes a support for a conventional high pressure liquified gas cylinder, typically containing carbon dioxide. A toggle mechanism brings the piercable seal on the cylinder against a needle so as to pierce the seal and admit fluid from the cylinder into the needle, from which it passes through an on-off valve, through a pressure regulation assembly to reduce pressure to the desired gas pressure, typically 12 psi. In the preferred embodiment, the mechanism for piercing the cylinder seal is built into the container lid, so that piercing is accomplished as the lid is closed. The on-off valve preferably includes a lid latch interlock, so that the lid cannot be opened unless the valve is off, preventing release of gas from the cylinder to the atmosphere.

Gas from the pressure production container is passed through a tube to a pressure chamber sized to hold one or more flexible medical fluid bags with sufficient gas volume around the bag or bags. The chamber includes a sealed lid for replacement of the bag and a tube passing through the chamber wall for egress of medical fluid from the bag.

The medical fluid passes to a binary valve having channels and flow restrictors permitting easy and convenient selection of any of a number of pre-selected output flow rates by simply rotating a valve to align a pointer with appropriate flow rate indicia.

This system is sturdy, inexpensive, convenient, and provides precise selection of any of a number of preselected, exact flow rates. Components such as the medical fluid bag, tubes and the flow control valves may be disposable, if desired. The system may be made up of plural components easily carried on the person. No particular location or orientation of any component is required. Alternatively, all components could be included in one easily portable overall container if desired.

BRIEF DESCRIPTION OF THE DRAWING

Details of the invention, and preferred embodiments thereof, will be further understood upon reference to the drawing, wherein.

DETAILED DESCRIPTION OF PREFERRED EMBODIMENTS

Figure 1:
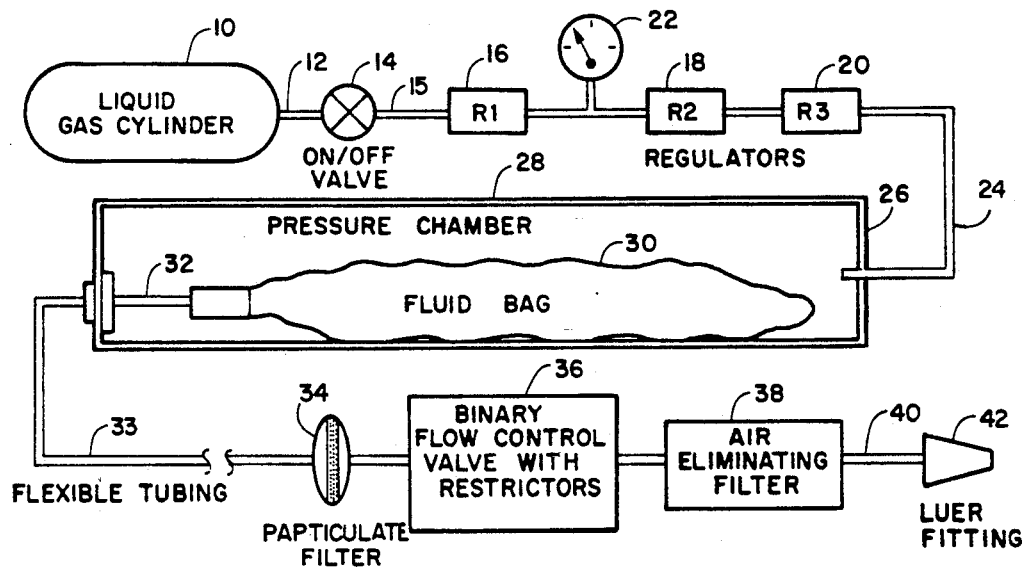
FIG. 1 is a schematic diagram of the overall system.

Referring now to FIG. 1, there is seen a schematic diagram of the overall medical fluid delivery system of this invention. A conventional high pressure liquid gas cylinder, typically a small carbon dioxide cylinder 10 at a pressure of about 1000 psi has a seal (not shown) at one end which is pierced by a needle 12, admitting pressurized fluid to on-off valve 14. Cylinder 10 typically contains about 25 grams of liquid carbon dioxide, providing enough energy to administer several normal infusions before needing replacement. Fluid from valve 14 passes through tube 15 to a first pressure regulator 16, preferably a needle valve type regulator, which typically reduces pressure to about 100 psi. The gas then passes to a series connected second regulator 18 which typically reduces pressure to about 30 psi and finally to third series regulator 20 where pressure is reduced to a very stable 12 psi. A relatively high working pressure of 12 psi is utilized to reduce flow variability due to output head pressure changes. A gauge 22 is provided to indicate when gas cylinder 10 is getting low and needs replacement.

Gas under pressure passes through tube 24 to pressurize pressure chamber 26. A conventional tightly sealing lid 28 is opened and a conventional flexible bag 30 filled with the selected medical fluid is placed in container 26 and connected to outlet tube 32. The shape and volume of chamber 26 is selected in accordance with the bags 30 to be used, assuring sufficient volume around the bag to provide uniform pressure application. Typical such bags 30 have dimensions of about 4.5 by 6.5 by 1.75 inches. This rectangular shape lens itself to being easily carried, clipped to a belt or attached by straps to allow patient mobility. If desired, chamber 26 may be sufficiently large to allow two or more bags 30 to be contained and pressurized. Each bag would have its own outlet 32 and downstream components, as described below. For example, one patient might require one fluid bag administering a saline solution with pharmaceuticals into a vein through a hypodermic needle while fluid from a second bag, at a second flow rate, is supplying nutrient solutions to the stomach through a nasal tube. Also there are situations where incompatible drugs may be delivered to the patient via two different administration sets and joined at the injection site.

Flexible tubing 33 is secured to outlet 32 and caries fluid from bag 30 to a particulate filter 34 which is preferably included to prevent any fine particles from reaching binary flow rate regulation assembly 36, as described in detail below. Fluid flowing at the rate selected at assembly 36 then passes to an air eliminating filter 38. Filter 38 is preferably included to provide assurance that no air is infused if the user has inadvertently neglected to purge out all of the trapped air in bag 30 when it is installed in chamber 26. This conventional filter includes a hydrophobic surface which holds back liquid while allowing the air to escape. Filter 38 may be integrated into flow rate regulation assembly, if desired.

Finally, the fluid passes through flexible tube 40 to any suitable fitting for connection to the infusion device, e.g., hypodermic needle, catheter or the like. A conventional male Leur fitting 42 with sterility cap is preferred. All flexible tubing used in this system is preferably flexible transparent plastic tubing which does not interact with fluids passing through and which has a bore diameter of about 0.020 inch and a wall thickness to bore ratio of no less than about 2:1 to reduce potential flow restrictions caused by tubing kinking.

Figures 2, 3:
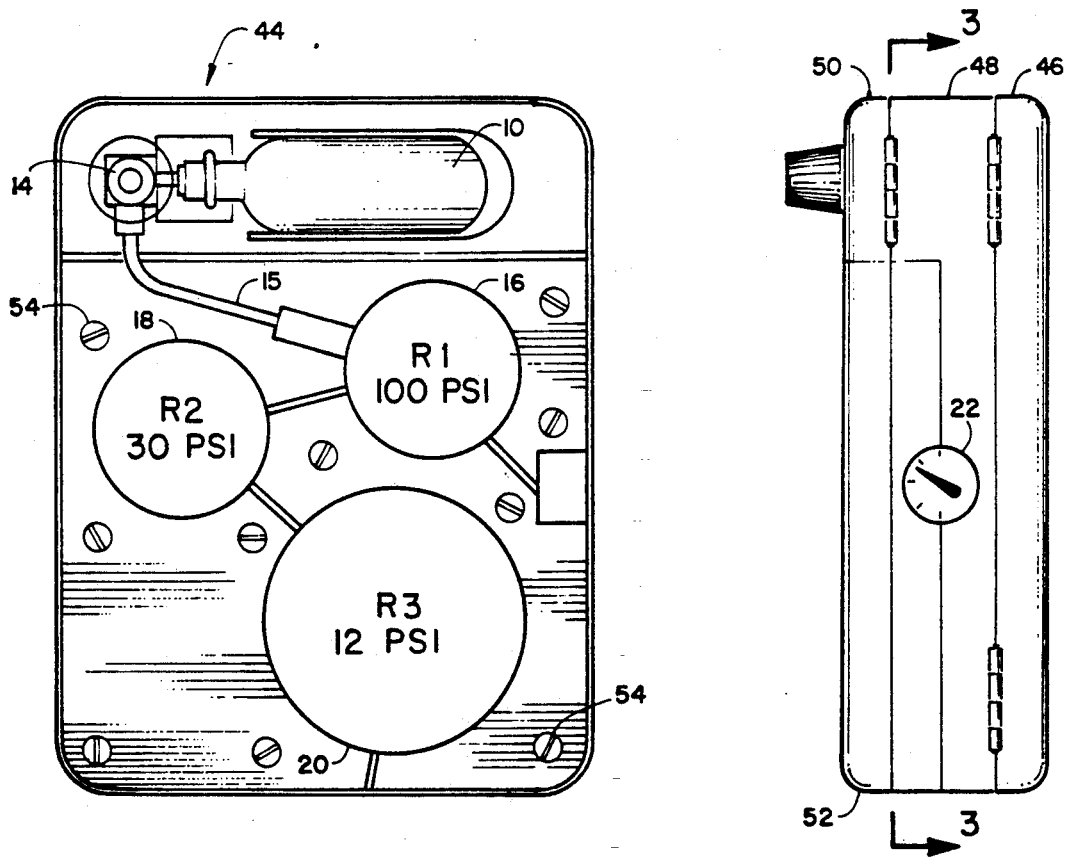
FIG. 2 is a side elevation view of the pressure production container.
FIG. 3 is a section view of the pressure production container taken on line 3—3 in FIG. 2.
Figure 4:
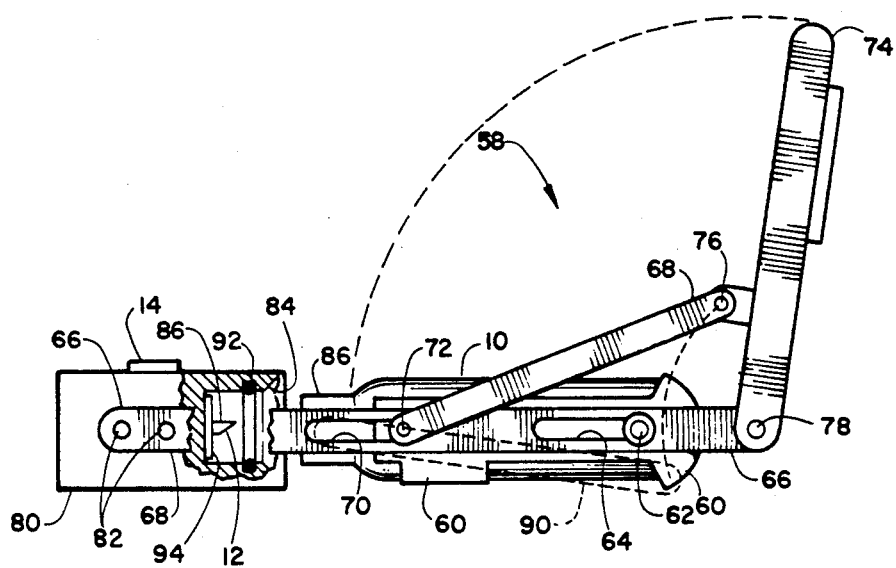
FIG. 4 is a schematic elevation view of toggle gas cylinder piercing mechanism.

Pressure production container 44 as seen in FIGS. 2 and 3, is basically a rectangular box, having a hinged bottom lid 46, a body 48, and a hinged narrow upper lid 50 over gas cylinder 10 and valve 14. The main upper section of container 44 is closed by panel 52 held to body 48 by a plurality of screws 54. Cylinder 10 is pierced by a needle on valve 14 (as shown in FIG. 4, discussed below). Fluid passes from cylinder 10 through valve 14, tube 15, first regulator 16, second regulator 18, third regulator 20 and an outlet indicated at 56, as detailed above. A gauge 22 measures pressure between regulators 16 and 18.

A toggle and piercing mechanism 58 adjacent to cylinder 10 (not shown in FIG. 3) is shown in schematic elevation in FIG. 4. A cradle 60 is adapted to receive and support cylinder 10. A headed pin 62 is secured to cradle 60 and slidably engages a slot 64 in a tie bar attachment 66. A toggle bar 68 is similarly slidably connected to a slot 70 in tie bar 66 through a headed pin 72. Toggle bar 68 is rotatably secured to a lever 74 by pin 76, with the end of lever 74 rotatably connected to the end of tie bar 66 through pin 78. The distal end of tie bar 66 is rigidly fastened to block 80 by fasteners 82, which may be bolts, rivets, screws or the like within a cavity 84 in block 80 is a needle 86 which communicates with valve 14 within block 80, as described above.

Operation of toggle and piercing mechanism 58 is begun by placing a cylinder 10 in cradle 60 with the seal end 86 towards needle 12. The end of lever 74 follows the path schematically indicated by broken line 88, with toggle bar 68 moving from the position shown in solid lines to the position shown in broken lines at 90. Cradle 60 is moved to the left, forcing the seal 86 against needle 12, piercing the seal and allowing pressurized fluid to flow toward valve 14. A pair of O-ring seals 92 and 94 engage the side and end of seal end 86 to prevent leakage of fluid.

Figure 5:
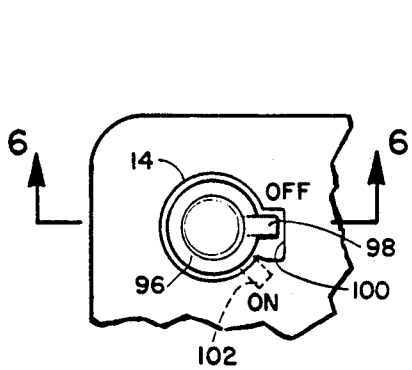
FIG. 5 is a detail plan view of the door/valve interlock mechanism.
Figure 6:
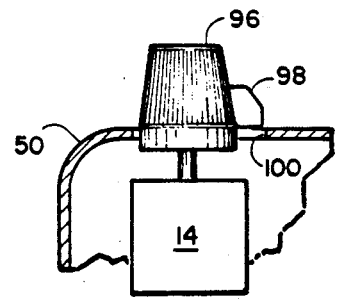
FIG. 6 is a detail section view of the door/valve interlock mechanism, taken on line 6—6 in FIG. 5.

In order to prevent inadvertent loss of pressure, at one of the pressure regulators or another fitting allowing pressure in pressure chamber 26 to be dissipated an interlock arrangement is provided between means for latching lid 50 closed and valve 14. As seen in FIGS. 5 and 6, a knob 96 on valve 14 extends upwardly through lid 50. A finger 98 on knob 14 will fit through a slot 100 only when knob and valve are in the "off" position. Lid 50 is closed with valve 14 off, then knob 96 is moved to the "on" position, with finger in the position shown in broken lines at 102, which latches lid 50 against opening. The lid cannot be opened without moving valve 14 to off.

Figure 7:
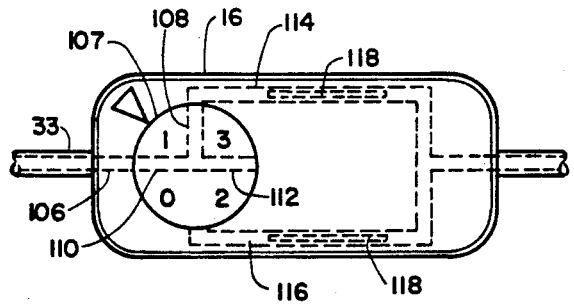
FIG. 7 is a schematic plan view of a first embodiment of a binary flow rate control valve.

Binary flow control valve 16 is capable of permitting any one of several very precisely set flow rates to be selected. FIG. 7 is a schematic representation of a flow control valve 16 in which the user may select "off" or any of three built-in flow rates. Fluid enters valve 16 through tube 33, entering channel 106. A communicating "T" shaped channel having three ends 108, 110 and 112 is formed in rotatable valve rotor 107. Two outlet channels 114 and 116 in the valve body engage valve rotor 107 at 90° to the inlet. Thus valve rotor 107 can be rotated to bring inlet 106 into fluid communication with either outlet 114 or 116, or with both outlets 114 and 116, or with neither (the "off" position). Two different, selected, conventional microporous restrictors 118 are located in outlet channels 14 and 116, each providing a different selected flow rate, or an additive flow rate when both are connected. Thus, a desired flow rate can be obtained from those provided easily and precisely, with no skill required to set a correct rate.

Figure 8:
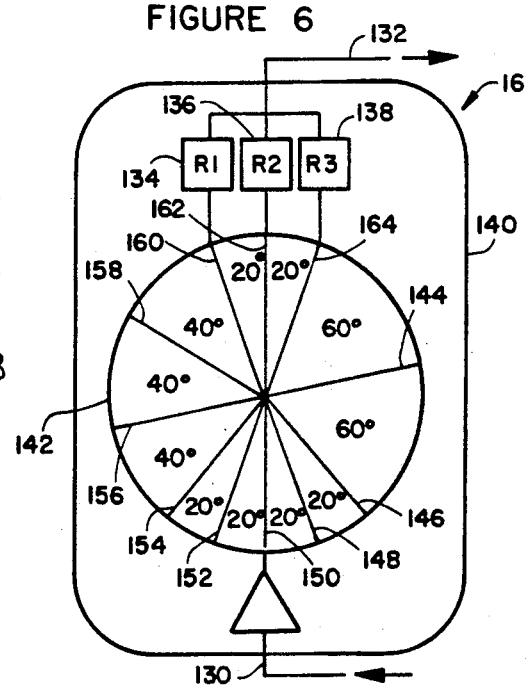
FIG. 8 is a schematic plan view of a second embodiment of a binary flow rate control valve.

A second embodiment of a binary flow control valve 16 which permits a much greater choice of flow rates is schematically represented in FIG. 8. Here, fluid enters through one channel 130 and exits through one channel 132 which collects any flow passing through restrictors 134, 136 and 138 located in valve body 140. Valve rotor 142 includes a plurality of channels 144-164, spaced apart the number of degrees shown and all communicating at the center of rotor 142. With this arrangement, with restrictor 134 alone providing a flow rate of 15 ml/hr, restrictor 136 providing 30 ml/hr and restrictor 138 providing 60 ml/hr. a wide range of flow rates may be precisely selected. For example, inlet 130 connected to channel 154, the flow rate will be 15 ml/hr; with channel 156, 30 ml/hr; with channel 152, 45 ml/hr; with channel 158, 60 ml/hr; with channel 146, 75 ml/hr; with channel 148, 90 ml/hr; with no channel connected, no flow and with channel 150 connected as shown in FIG. 8, all restrictors will receive flow and the maximum flow rate of 105 ml/hr is achieved. Thus, a user under the direction of his physician can easily and accurately adjust the flow rate to meet changing conditions.

While certain particular materials, conditions and arrangements were detailed in conjunction with the above description of preferred embodiments, those can be varied, where suitable, with similar results. Other variations, applications and ramifications of the present invention will occur to those skilled in the art upon reading the present disclosure. Those are intended to be included within the scope of this invention, as defined in the appended claims.

I claim:

1. A medical fluid delivery system which comprises:
   a first container adapted to hold a high pressure liquid gas cylinder of the sort having a piercable seal at one end;
   a piercing needle located adjacent to the cylinder in said container:
   means for moving said needle and cylinder together so that said needle pierces said seal permitting high pressure fluid to enter said needle:
   an on-off valve receiving fluid from said needle, said on-off valve includes a knob rotatably with said valve between off and on positions, said knob adapted to extend outwardly of a container lid, said knob having an outwardly extending finger and said lid having a hole and slot arranged so that said knob and finger can pass through said slot only when said valve is in the off position, and said knob being rotatable to the on position with said lid closed, whereby said finger then overlaps a portion of the lid, latching said lid in the closed position;
   pressure regulation means adapted to receive fluid from said valve and reduce pressure to a selected gas pressure level:
   a gas tube conveying gas from said pressure regulation means to a pressure chamber:
   said pressure chamber adapted to contain at least one flexible medical fluid containing bag filling part of the pressure chamber volume:
   an outlet tube selectively connectable to said medical fluid bag passing through the pressure chamber walls
   a binary flow control means connected to said outlet tube and adapted to control fluid flow rate: and
   means adapted to connect the outlet of said flow control means to a patient administration means.

2. The medical fluid delivery system according to claim 1 wherein said means for moving said needle and cylinder together to pierce said seal comprises:
   a cradle for supporting said cylinder with said seal extending toward said needle;
   at least one tie bar secured to means supporting said needle and extending along said cradle;
   said cradle mounted for sliding movement along said tie bar;
   a lever pivotably at the end of each tie bar; and
   a toggle bar extending from said cradle to a connection intermediate the ends of said lever;
   whereby movement of said lever toward said needle support drives said cradle toward said needle support and said seal into piercing engagement with said needle.

3. The medical fluid delivery system according to claim 2 further including seal means adapted to seal between the seal end of said cylinder and said needle support and to seal between the sides of said cylinder adjacent to said seal and said needle support.

4. The medical fluid delivery system according to claim 1 wherein said binary flow control means comprises:
   a rotatable valve rotor having at least two channels extending through the rotor in directions perpendicular to the axis of rotation;
   a valve body having a circular opening adapted to receive said rotor for rotation therein;
   an inlet channel extending from said outlet tube to said opening in juxtaposition to said rotor channels;
   at least two exit channels extending from openings in juxtaposition to said rotor channels to a single flow control outlet connection;

each of said exit channels containing flow restrictor means providing a different selected flow rate;

whereby rotation of said rotor to selected positions connects said inlet to selected one or more exit channels;

whereby any of a provided number of precise outlet flow rates may be selected.

5. The medical fluid delivery system according to claim 1 further including an in line particulate filter upstream of said binary flow control means.

6. The medical fluid delivery system according to claim 1 further including an air eliminating filter in the line downstream of said binary flow control means.

7. A medical fluid delivery system which comprises:
(a) a first production and regulation container comprising:
   a cradle adapted to hold a high pressure liquid gas cylinder of the sort having a piercable seal at one end;
   a lid over said cradle to permit removal and replacement of said cylinder;
   a piercing needle located adjacent to the cylinder pierceable seal in said container; said cradle slidably attached to a bar member; a lever member pivotally attached to the bar member and connected to the cradle;
   means for moving said needle and cylinder together so that pivoting the lever member relative to the bar member moves the cradle and cylinder along said bar towards the piercing needle, causing said needle to pierce the seal at the end of the cylinder permitting high pressure gas to enter said needle;
   an on-off valve receiving fluid from said needle;
   pressure regulation means adapted to receive fluid from said valve and reduce pressure to a selected gas pressure level;
   a gas tube conveying gas from said pressure regulation means to a pressure chamber;
(b) said pressure chamber comprising:
   a box adapted to contain at least one flexible medical fluid containing bag filling part of the pressure chamber volume;
   a sealable lid removable for replacement of said bag;
   an outlet tube selectively connectable to said medical fluid bag passing through the pressure chamber wall to a binary flow control assembly;
(c) said binary flow control assembly comprising:
   means for selecting any of a plurality of pre-set fluid flow rates; and
(d) means adapted to connect the outlet of said flow control means to a patient administration means;
   each of said pressure production and regulation container, pressure chamber and binary flow control assembly being a unitary structure connected by tubing.

8. The medical fluid delivery system according to claim 7 wherein:
said on-off valve includes a knob rotatable with said valve between "off" and "on" positions, said knob adapted to extend outwardly of said container lid;
said knob having an outwardly extending finger and said lid having a hole and slot arranged so that said knob and finger can pass through said slot only when said valve is in the "off" position; and
said knob rotatable to the "on" position with said lid closed, whereby said finger then overlaps a portion of the lid, latching said lid in the closed position.

9. The medical fluid delivery system according to claim 7 wherein said binary flow control assembly comprises:
a rotatable valve rotor having at least two channels extending through the rotor in directions perpendicular to the axis of rotation;
a valve body having a circular opening adapted to receive said rotor for rotation therein;
an inlet channel extending from said outlet tube to said opening in juxtaposition to said rotor channels;
at least two exit channels extending from openings in juxtaposition to said rotor channels to a single flow control outlet connection;
each of said exit channels containing flow restrictor means providing a different selected flow rate;
whereby rotation of said rotor to selected positions connects said inlet to selected one or more exit channels;
whereby any of a provided number of precise outlet flow rates may be selected.

10. The medical fluid delivery system according to claim 7 further including an in line particulate filter at the inlet of said binary flow control means.

11. The medical fluid delivery system according to claim 7 further including an air eliminating filter in the line at the outlet of said binary flow control means.

12. The medical fluid delivery system according to claim 7 wherein said pressure chamber is adapted to hold at least two fluid bags, and each bag is provided with its own set of outlet tube, binary flow control assembly and means to connect the outlet of the flow control assembly to a patient administration means.

* * * * *